United States Patent [19]

Sussman et al.

[11] Patent Number: 5,155,019
[45] Date of Patent: Oct. 13, 1992

[54] DETECTION OF THE PRESENCE OF BIOLOGICAL ACTIVITY IN A SEALED CONTAINER UTILIZING INFRARED ANALYSIS OF CARBON DIOXIDE AND APPARATUS THEREFOR

[75] Inventors: Mark L. Sussman, Baltimore; Joseph E. Ahnell, Hydes; Laurence R. McCarthy, Baltimore, all of Md.

[73] Assignee: Becton, Dickinson and Company, Franklin Lakes, N.J.

[21] Appl. No.: 225,561

[22] Filed: Jul. 28, 1988

Related U.S. Application Data

[63] Continuation of Ser. No. 686,327, Dec. 12, 1984, abandoned, which is a continuation of Ser. No. 414,235, Aug. 31, 1982, abandoned.

[51] Int. Cl.⁵ .......................... C12Q 1/04; C12M 1/34
[52] U.S. Cl. .......................... 435/34; 435/39; 435/291; 435/807; 435/808; 436/164; 436/165; 250/343; 250/576; 356/437; 422/82.05; 422/82.09
[58] Field of Search ............ 435/4, 6, 29, 32, 33, 435/34, 39, 173, 289, 291, 807, 808, 822, 253.6, 252.1, 31; 436/164, 165; 422/80, 82.05, 82.09; 356/51, 437, 438, 439; 250/343, 573, 576

[56] References Cited

U.S. PATENT DOCUMENTS

| | | | |
|---|---|---|---|
| 2,269,674 | 1/1942 | Liddel et al. | 436/164 X |
| 3,322,956 | 5/1967 | Shah | 435/39 X |
| 3,454,759 | 7/1969 | Calhoun | 250/43.5 |
| 3,676,679 | 7/1972 | Waters | 250/380 |
| 3,935,073 | 1/1976 | Waters | 435/14 |
| 4,073,691 | 2/1978 | Ahnell et al. | 435/34 |
| 4,101,383 | 7/1978 | Wyatt et al. | 435/7 X |
| 4,182,656 | 1/1980 | Ahnell et al. | 435/34 |
| 4,220,715 | 9/1980 | Ahnell | 435/34 |
| 4,323,956 | 4/1982 | Prustka | 362/306 |
| 4,372,683 | 2/1983 | Sternberg | 435/291 X |
| 4,889,992 | 12/1989 | Hoberman | 250/343 |

OTHER PUBLICATIONS

Collier, C. R. et al, *Jour. of Lab. and Clin. Med.*, vol. 45(4), pp. 526-539 (1955), "Continuous Rapid Infrared CO₂ Analysis".
Threlkeld, C. H., *Jour. of Food Science*, vol. 47, pp. 1223-1226 (1982), "Detection of Microbial Contamination Utilizing an Infrared CO₂ Analyzer".
*Chemical Abstracts*, vol. 82, p. 733 (1975), Abstract No. 67867z: Garza, A. C. et al, "Apparatus and Method for Determining Oxygen and Carbon Dioxide in Sealed Containers".
*Chemical Abstracts*, vol. 86, p. 245 (1977), Abstract No. 117528v: Boyle, D. T., "A Rapid Method for Measuring Specific Growth Rate of Microorganisms".
*Chemical Abstracts*, vol. 86, p. 345, Abstract No. 104445r (1977): Wheldon, A. G. et al; "An Instrument for Detecting Carbon Dioxide".
*Glass Engineering Handbook*, Shand, E. B. et al, McGraw-Hill Book Co., Inc., New York, pp. 30-33 (1958).
White, J. R., *The Invisible World of The Infrared*, Dodd, Mead & Co., Book Jacket and pp. 36, 42 (1984).

*Primary Examiner*—David L. Lacey
*Assistant Examiner*—William H. Beisner
*Attorney, Agent, or Firm*—Aaron Passman

[57] ABSTRACT

A method and apparatus for detecting the presence of biological activity in a sample of material. In the method, a sample of the material is placed in a closed container with a growth medium which includes a carbon source which may be metabolized to produce carbon dioxide. The medium with the sample therein is exposed to conditions conducive to the occurrence of normal metabolic process for a period of time sufficient to cause production of $CO_2$ by the metabolism of the carbon source. Thereafter, the presence of $CO_2$ in the gaseous atmosphere above the medium is detected by measuring the infrared absorbance of the gaseous atmosphere with the container by passing an infrared beam through the container and the gaseous atmosphere and detecting the infrared absorbance of the gaseous atmosphere.

11 Claims, 8 Drawing Sheets

DETECTION OF THE PRESENCE OF BIOLOGICAL ACTIVITY IN A SEALED CONTAINER UTILIZING INFRARED ANALYSIS OF CARBON DIOXIDE AND APPARATUS THEREFOR

This application is a continuation of application Ser. No. 686,327, filed Dec. 12, 1984, now abandoned, which is a continuation of application Ser. No. 414,235, filed Aug. 31, 1982, now abandoned.

BACKGROUND OF THE INVENTION

1. FIELD OF THE INVENTION

The present invention relates generally to a method and apparatus for detecting biological activity. More particularly, the present invention relates to a method for making rapid analysis of materials in which the presence of microorganisms or the like is suspected by infrared analysis of the head space of a container holding a growth medium which may be metabolized to provide a gaseous product.

When, for example, bacteria are cultured in a suitable medium including a carbon source, such as glucose, the carbon source is broken down to form $CO_2$ during the growth and metabolism of the bacteria. It would be desirable to provide a direct non-invasive method for the analysis of the gaseous atmosphere produced over the growth medium in the head space in order to determine the presence or absence of biological activity.

2. Description of the Prior Art

Techniques have been developed for detection of bacteria which involve incubating a sample of material to be tested in a closed container with a radioisotope-labeled culture medium and monitoring the atmosphere produced in the container to determine whether or not radioactive gases are produced. A system of this type is disclosed in U.S. Pat. Nos. 3,676,679 and 3,935,073. Such systems are rapid and reliable but they have a number of disadvantages. Radioactive labeled materials are expensive and require special handling during storage, use and disposal. Moreover, such systems generally require the invasion of the head space above the growth medium to remove a sample of the gas produced by the microorganism to a separate sampling and detection chamber. However, the use of radioactive isotopes and instrumental systems has generally been considered necessary in order to detect the minute quantities of metabolic product gases produced in a relatively short period of time so as to detect the presence of biologically active species.

U.S. Pat. No. 4,182,656 describes a further method for detecting the presence of biologically active agents, such as bacteria, by monitoring the metabolic products of the biologically active agent in the head space of a container of a growth medium and the biologically active agent. In this method, a sample of material to be tested for the presence of biologically active agents is introduced into a sealable container partially filled with a culture medium comprising a $^{13}C$- labeled substrate which may be metabolized by the biologically active agent. The remainder of the container is filled with a culture gas. The container and its contents are subjected to conditions conducive to biological activity for a predetermined period sufficient for metabolism of the medium to produce carbon dioxide. Thereafter, the ratio of $^{13}CO_2$ to $^{12}CO_2$ in the culture gas in the container is determined and compared to the initial ratio of $^{13}CO_2$ to $^{12}CO_2$ in the culture gas in order to detect any differences which would indicate the presence of biologically active agents in the sample. This method also requires invasion of the head space in the container to remove a sample for the comparison testing.

There exists a need for a practicable, non-radioactive system for measuring metabolically produced gases without invasion of the container to remove a sample of the head space gas in order to detect bacteria and the like.

Accordingly, it is a principal object of the present invention to provide a rapid method for detecting the presence or absence of biologically active agents in a substance contaminated with the biologically active agent.

Another object of the invention is to provide a method for detecting the presence or absence of biologically active agents which uses comparatively inexpensive apparatus and materials.

It is a further object of the present invention to provide an instrumental method for detecting the presence or absence of biologically active agents which does not require the removal of a sample of the head space gas from a container containing a fermented sample and a growth medium.

Another object of the present invention is to provide an instrumental system for detecting the presence or absence of biologically active agents which does not require the use of radioactive materials.

Further objects of the invention will become apparent from a consideration of the following description and the appended claims.

SUMMARY OF THE INVENTION

The objects of the invention are achieved by providing a method for detecting the presence of biologically active agents comprising the steps of providing a sealed, sterile container partially filled with a sterile culture medium. The container further contains a sample of material to be tested for biological activity. The remainder of the container is provided with a suitable gaseous head space for the suspected biological material. The sealed container and its contents are then subjected to conditions conducive to biological activity for a predetermined period of time sufficient for metabolism of the culture medium to produce a gaseous product which can be detected by infrared spectroscopy. In most cases the gaseous product will be $CO_2$. Thereafter the $CO_2$ is detected by scanning the head space through the sidewall of the container with an infrared spectrophotometer and comparing the spectrophotometric analysis with a reference transmittance obtained by scanning the head space containing ambient air.

In the most preferred embodiment, the invention involves providing a sterile, sealable container partially filled with a sterile culture medium comprising a substrate which may be metabolized to produce $CO_2$, the remainder of the container being filled with a suitable head space gas. A sample of the material to be tested for biological activity is introduced into the container and the container is sealed. The sealed container and its contents are then subjected to conditions conducive to biological activity for a predetermined period of time sufficient for metabolism of the substrate to produce $CO_2$ if a biologically active agent is present. The carbon dioxide is then detected by passing an infrared beam completely through the sidewall of the container and the head space gas. The infrared beam is passed through the container at a level clear of the culture medium so as to permit the beam to intercept the head space gas over the culture medium.

DETAILED DESCRIPTION OF THE PREFERRED EMBODIMENTS

Figure 1:
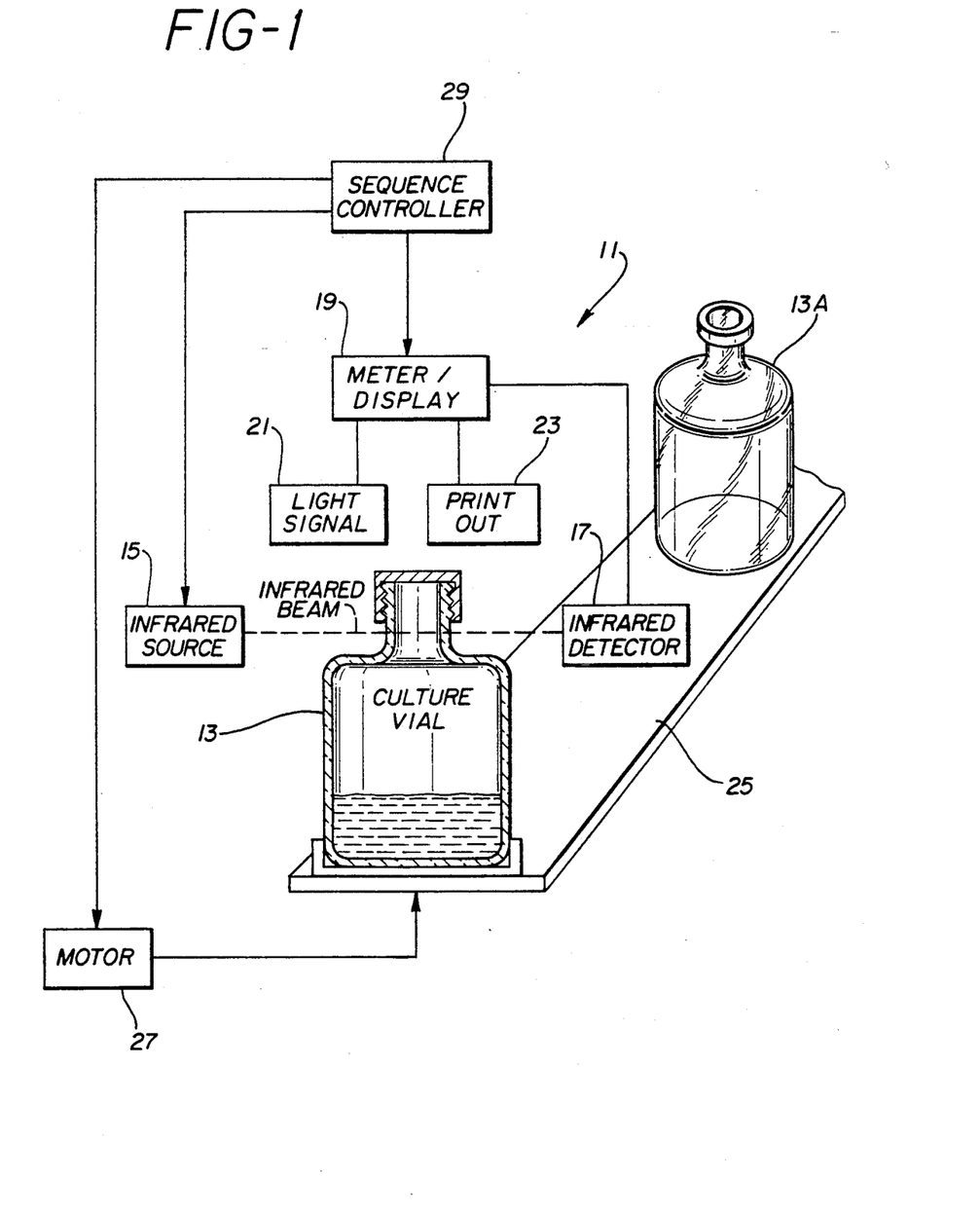
FIG. 1 is a schematic diagram of apparatus useful in the present invention.

A detector apparatus embodying the principles and concepts of the invention is designated in FIG. 1 by the numeral 11. Apparatus 11 is particularly useful in providing early detection of the general presence of most medically significant bacteria in materials such as blood, urine, spinal fluid, water samples and the like. The presence of such bacteria is detected by measuring the amount of $CO_2$ generated when a material to be analyzed is placed into a growth medium including a carbon containing source, such as a glucose, which is metabolized or fermented by the bacteria to produce $CO_2$ following incubation of the sample therein. The presence of $CO_2$ in the atmosphere above the growth medium is an indication of the presence of microorganisms in the original sample of material. In the apparatus of the present invention the presence of $CO_2$ in the head space above the growth medium is detected by passing an infrared beam through the sidewall of the container and detecting the infrared absorbance in the head space gas within the container.

A sample to be analyzed, such as blood or urine or the like, is placed into a sterile culture container 13 together with a growth medium suitable for organism metabolism to produce $CO_2$. Thereafter the sample is incubated in the culture vial. At suitable intervals the culture vial is transferred to an infrared measuring means which includes an infrared source 15 and an infrared detector 17. The infrared absorbance within the head space of the culture vial is detected and may be displayed on a meter 19 which may include provision for simultaneous display of a light signal 21 and a computer printout 23.

The culture vial 13 is located on a track 25, which may be linear, circular, or of serpentine geometry to provide easy positioning of the culture vial 13 between the infrared source and the infrared detector. A second culture vial 13 A is shown in phantom outline in position waiting to be tested by infrared source 15 and infrared detector 17. A motor 27 is provided to activate the track 25. A sequence controller 29 is used to properly sequence activation of the motor 27, the infrared source 15 and the meter display 19. It may sometimes be desirable to provide means for rotating the culture vial during activation of the infrared source to provide compensation for uneven sidewall thickness.

The non-invasive method of the present invention to detect and quantitate changes in head space gas concentrations of metabolically produced gases, such as carbon dioxide, by passing an infrared beam completely through the container for the suspect material in a liquid culture medium has important applications for the development of an automated system for the detection of biological activity, particularly as related to bacterial growth. The infrared beam is passed through the vial at a level clear of the liquid culture medium, which permits the beam to intercept the head space gas over the surface. This non-invasive technology differs substantially from methods previously used for detection of metabolically produced gases, such as the detection of radioactive $C_{14}$. No gas is transferred to or from the vial and no invasive probe is used for the measurement of any parameter of the culture gas. There is no need for any penetration of the vial septum. Such non-invasive technology has several advantages over previously used methods, among which are:

- there is no possibility of contamination caused by needle or probe penetration of the vial septum;
- the design of an automated apparatus is simplified, in that there is no need to provide provisions for a needle-carrying head assembly or other invasive sampling apparatus;
- the necessity of replacing flushed head space gas with sterile culture gas is eliminated;
- the use of special culture gases is not required;
- faster vial sampling is possible, since only vial positioning is involved; no vertical head motion is necessary;
- the cost of culture media raw materials is reduced due to the elimination of any radiolabeled substrate; and
- all radioisotopes are eliminated, which eliminates the problems of shipping, handling and storing low level radioisotopes.

The culture container must have a "window" for infrared transmittance with a bandwidth suitable for detecting the gaseous product of metabolism. For $CO_2$ the bandwidth required includes wave numbers from about $2400 CM^{-1}$ to $2300 CM^{-1}$. The infrared transmittance of the container within the gaseous product absorbance bandwidth must be at least about 1 percent to be useful to detect the gaseous product via infrared analysis.

It has been discovered that various types of glass vials and a particular type of plastic vial are useful in the practice of the present invention. In particular, borosilicate glass vials and soda lime glass vials have been found to be useful. It has also been determined that polymethylpentene plastic provides a transparent "window" at the analytical wavelength of $CO_2$.

It should be understood that those skilled in the art of infrared spectroscopy do not consider either glass or plastic to be of use as a sample-containing cell for infrared analysis. Glass, although transparent to visible light, becomes opaque to infrared wavelengths just slightly longer than those applicable to carbon dioxide analysis. Carbon dioxide has a strong infrared absorption at $2349 CM^{-1}$, free from water vapor interference.

Glass has not been considered in the infrared spectroscopy art as being suitable for infrared analysis of most organic compounds. Plastics, being organic materials, have infrared absorption bands throughout the usual infrared range of wave numbers $400 CM^{-1}$ to $4000 CM^{-1}$. It is surprising that polymethylpentene exhibits a slightly transparent "window" at $2349 CM^{-1}$ with enough transmission to permit the analysis of carbon dioxide. While not wishing to be bound by any theory, it appears that carbon dioxide absorbs infrared energy in a wave length region corresponding to the covalent triple bond of organic molecules. Triple bonds are not normally found in polymeric materials. Polymethylpentene is a preferred polymeric material containing covalent double bonds. For use as a culture vial, the polymeric material must also be capable of being sterilized, whether by conventional autoclave or gas or radiation sterilization techniques. Polymethylpentene is suitable in this respect in that it can withstand temperatures suitable to achieve sterility.

Typical culture media generally contain water, a carbon source, and a nitrogen source. The carbon source may be a carbohydrate, amino acid, mono- or dicarboxylic acid or salt thereof, polyhydroxy alcohol, hydroxy acid or other metabolizable carbon compound. Usually the carbon source will comprise at least one sugar such as glucose, sucrose, fructose, xylose, maltose, lactose, etc. Amino acids such as lysine, glycine, alanine, tyrosine, threonine, histidine, leucine, etc. also frequently comprise part of the culture media carbon source.

The nitrogen source may be nitrate, nitrite, ammonia, urea or any other assimilable organic or inorganic nitrogen source. An amino acid might serve as both a carbon and a nitrogen source. Sufficient nitrogen should be present to facilitate cell growth.

A variety of calcium, potassium and magnesium salts may be employed in the culture medium including chlorides, sulfates, phosphates and the like. Similarly, phosphate and sulfate ions can be supplied as a variety of salts. As such materials are conventional in fermentation media, the selection of specific materials as well as their proportions is thought to be within the skill of the art.

The so called minor elements which are present in trace amounts are commonly understood to include manganese, iron, zinc, cobalt and possibly others.

Due to the fact that most biologically active species cannot function in strongly acidic or strongly alkaline media, suitable buffers such as potassium or ammonium phosphates may be employed, if desired, to maintain the pH of the culture medium near neutral.

Examples of well known culture media which may be used in the present invention are peptone broth, tryptic soy broth, nutrient broth, thioglycolate broth, or brain-heart infusion broth.

At the outset of the process, the growth medium is inoculated with a sample of the material to be tested while the pH is maintained between about 6.0 and about 8.0 and desirably at about 7.2. The amount of sample employed may vary widely but preferably should be from about 1.0 to about 20 percent of the growth medium by volume. After a short delay, any organisms present will grow rapidly followed by a decrease in growth rate. In addition, the rate of metabolism and thereby the rate of evolution of $CO_2$ will vary depending upon such factors as nutrient composition, pH, temperature, proportion of inoculum, and type of organism present.

For effective metabolism for the majority of bacteria, the temperature of the medium with the sample therein is preferably maintained between about 35° C. and about 37° C. Some organisms achieve optimum growth at temperatures of 20° C. or lower while others may exhibit optimum growth at 45° C. or higher. This invention may employ any temperature best suited in a given circumstance. Although satisfactory growth can be achieved without agitation, metabolism preferably is carried out with active shaking, stirring, or the like, effective to insure proper evolution of $CO_2$ from the medium. In one preferred embodiment, agitation is provided by stirring to introduce a vortex into the liquid medium. An external stirring apparatus to provide the vortex is sometimes desirable.

Most often, interest will be in determining whether a given sample contains aerobic bacteria and, therefore, the atmosphere in the containers generally will contain oxygen. This invention can be used to detect anerobic bacteria, however, by insuring that head space gas oxygen content be minimal. If photoresponsive or phototoxic microorganisms are of interest, light should be provided or excluded accordingly.

Turning now more particularly to the mechanical equipment depicted in FIG. 1, the culture containers 13 and 13A preferably will have a total capacity of between 30 ml and 150 ml of which 2-100 ml will be occupied by the culture medium and test sample. The volume of blood or urine or other sample may be, for example, 0.1-10 ml. Smaller culture containers are sometimes useful for particular applications, such as microorganism identification and susceptibility testing, in which infrared detection of $CO_2$ may be useful.

The following examples illustrate various features of the present invention but are intended to in no way limit the scope of the invention which is defined in the appended claims. In particular, although the metabolic product of interest in the examples provided is carbon dioxide, other metabolically formed gases may be detected, provided an infrared absorption band exists for the compound and provided that the container material has a region of infrared transmittance of at least $+/-10$ $CM^{-1}$ at the absorption wavelength of the gaseous product with at least about 1 percent transmission at the wavelength region of interest.

EXAMPLE 1

Figure 2:
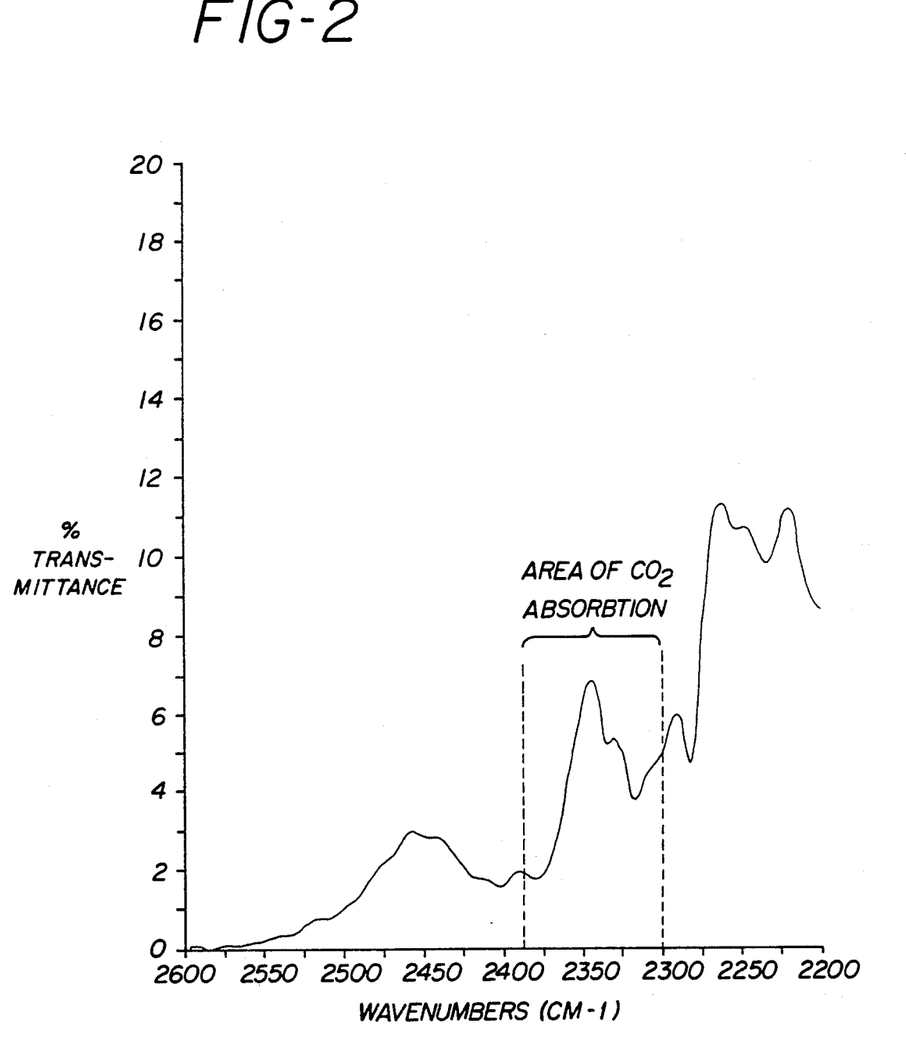
FIGS. 2 through 4 represent infrared scans of various plastic and glass materials in the form of a bottle or vial.
Figure 3:
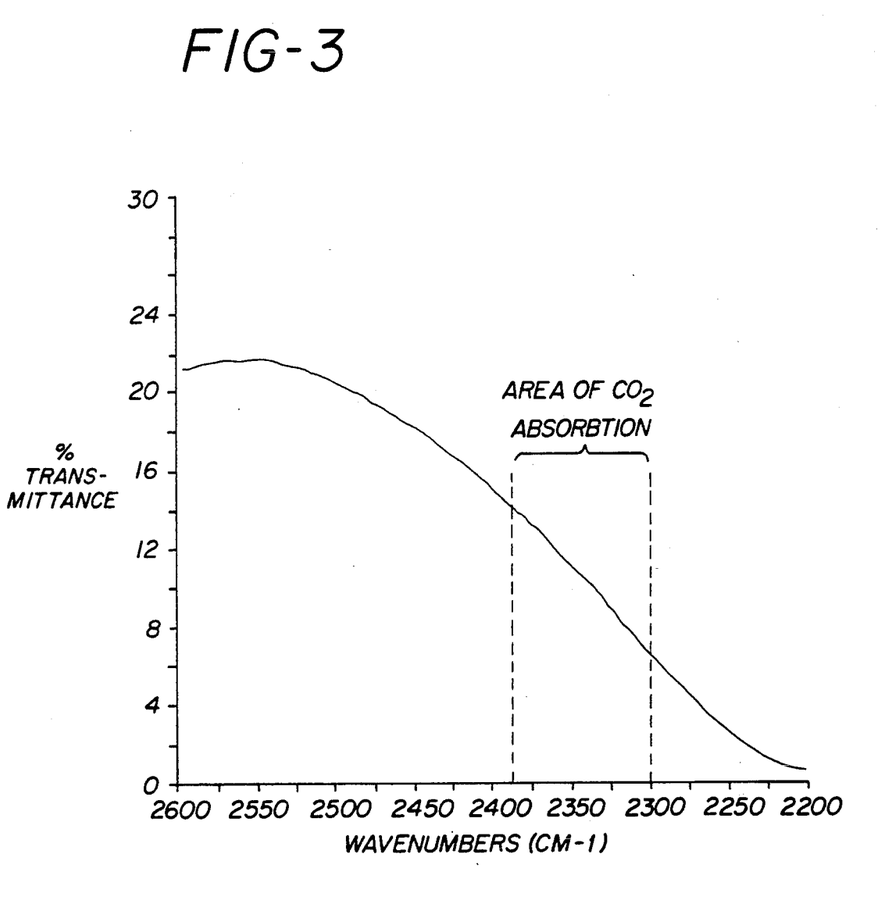
Figure 4:
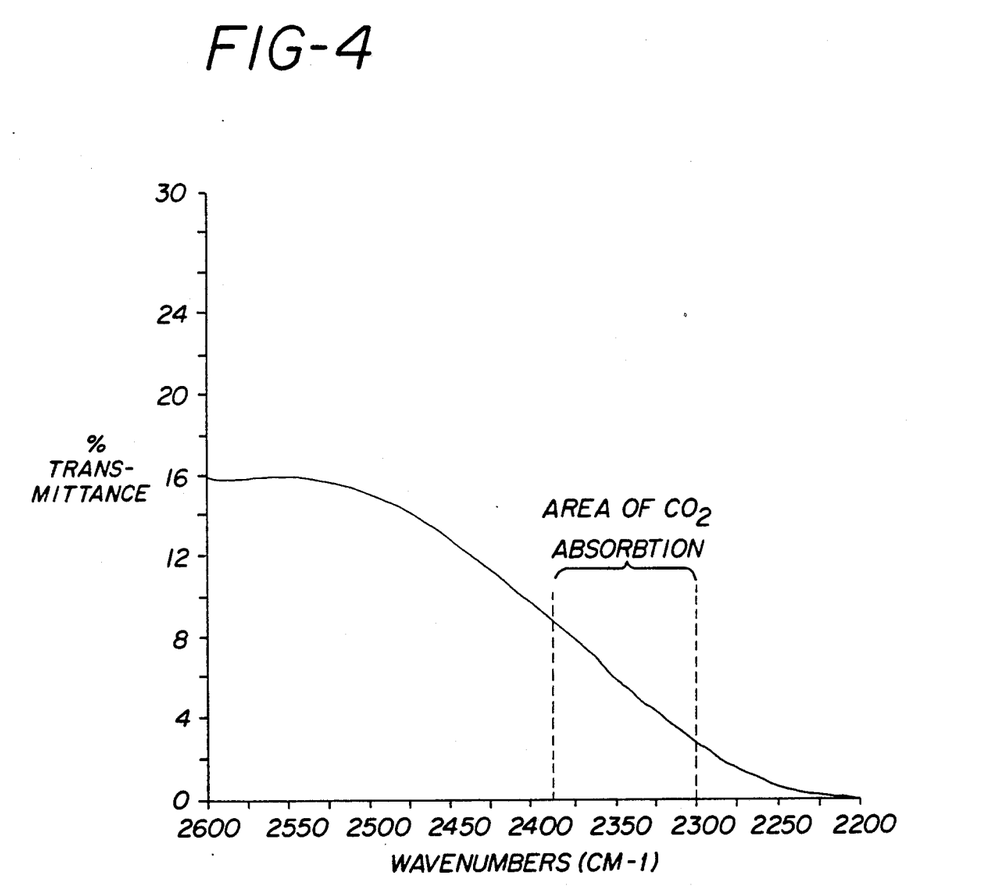

The relative amounts of infrared transmission through three different materials is shown in FIGS. 2 through 5. In FIG. 2, a 125 ml polymethylpentene bottle with a sidewall thickness of approximately 0.03 inches and an outside diameter of 1.88 inches is placed in the instrument and subjected to an infrared scan. The area of $CO_2$ absorption is outlined in FIG. 2. As indicated, the area of $CO_2$ absorption varies from a transmittance of from about 2 percent to about 7 percent. This is sufficient to permit a scan for $CO_2$ to be made. In FIG. 3, a tubing vial of borosilicate glass with a sidewall thickness of 0.053 inches and an outside diameter of 1.33 inches is scanned at the wave numbers of interest. As indicated, the transmittance of borosilicate glass in the infrared wave number region slightly beyond the area of $CO_2$ absorption is zero. The percent transmittance in the area of $CO_2$ absorption varies from about 7 percent to about 14 percent. In FIG. 4, a fifty mililiter bottle made of soda lime glass having an outside diameter of approximately 1.7 inches is scanned by infrared. Again, the percent transmittance at the infrared wave number slightly greater than that for $CO_2$ absorption are zero. In the area of $CO_2$ absorption the percent transmittance ranges from about 3 to about 9. All infrared scans in this example and other examples were made with a Nicolet 5-MX FT-IR spectrophotometer. The scans for FIGS. 2 through 5 were made with the vials opened to room air and are the result of the addition and averaging of sixty scans. The scans are referenced against the scan of room air, which was also scanned sixty times. In each case the area of interest in terms of carbon dioxide absorption is in the region between approximately 2400 to 2300 $CM^{-1}$.

EXAMPLE 2

Figure 5:
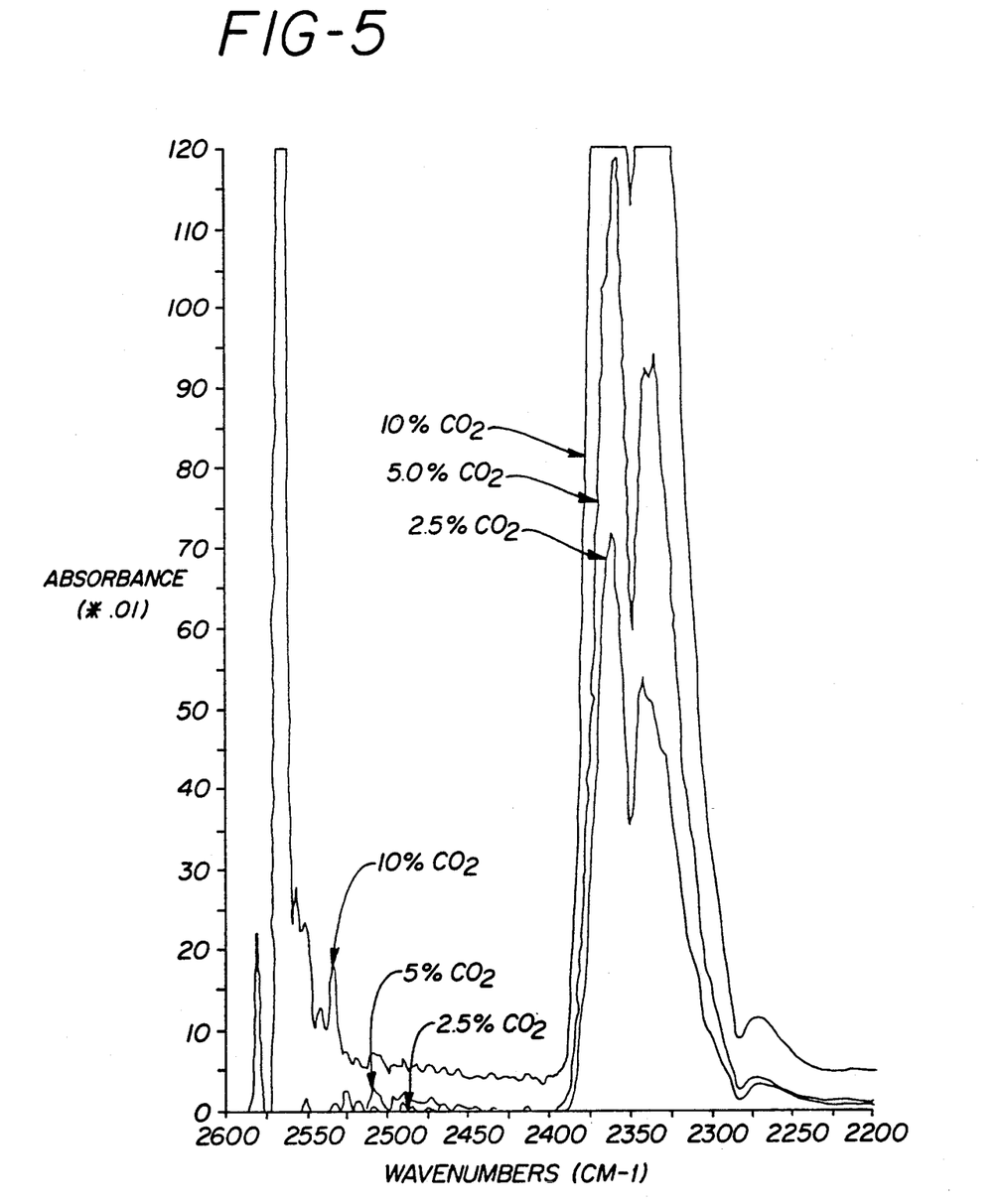
FIGS. 5 and 6 represent the infrared absorption scan of the head space of the various containers containing various levels of $CO_2$.
Figure 6:
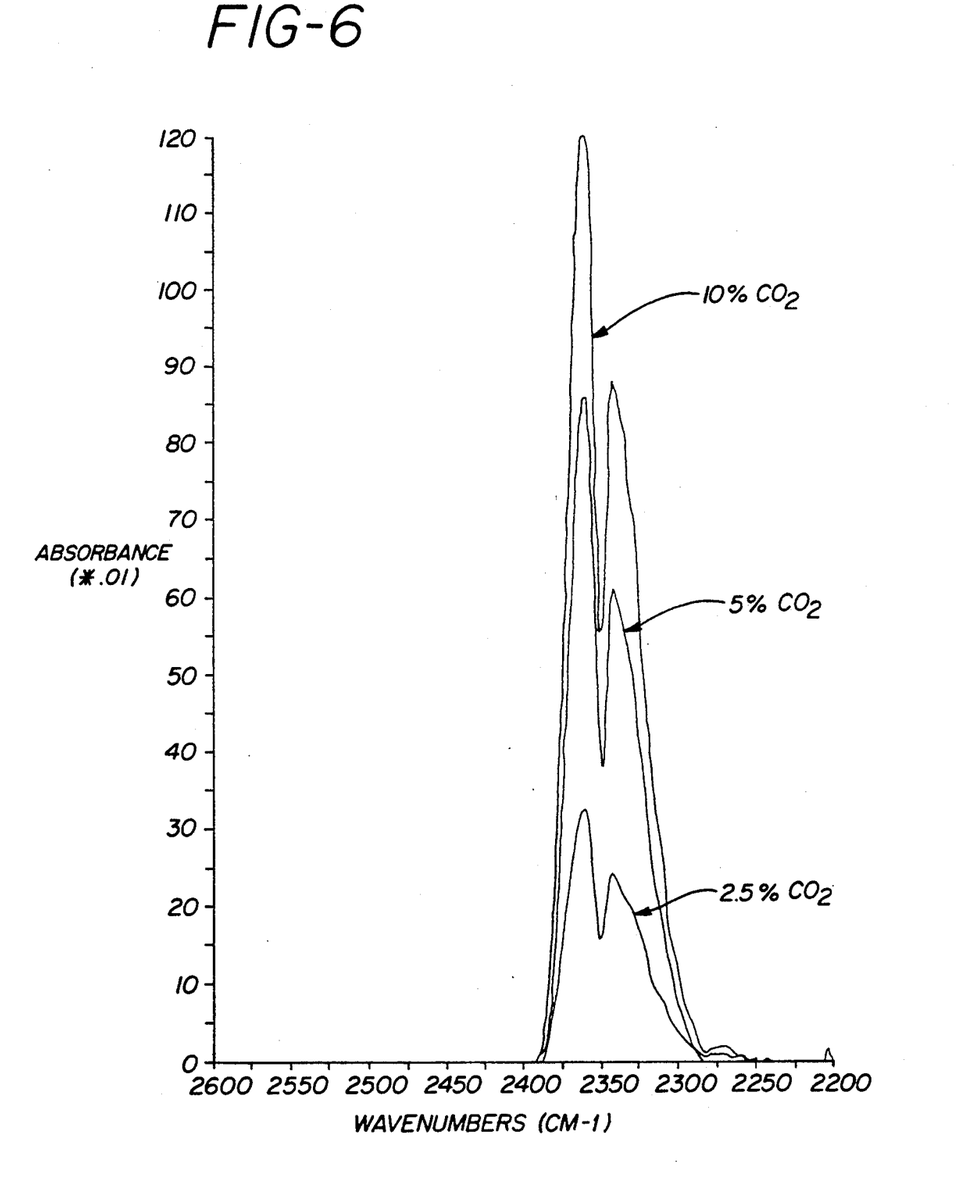

In FIGS. 5 and 6, various levels of carbon dioxide gas were provided in the head space of the polymethylpentene bottle and a borosilicate glass tubing vial. Reference scans of each container were first taken with the bottles opened to room air by taking sixty readings in the Nicolet spectrophotomer. The vials were then flushed with gases containing approximately 2.5 percent, 5.0 percent and 10.0 percent carbon dioxide and were then quickly sealed. The bottle and the vial were then again read following each flushing for sixty scans in the Nicolet spectrophotomer. The results are shown in FIGS. 5 and 6 with the vertical axis in this case being the infrared absorbance times 0.01. A clearer correlation can be seen between the increase in infrared absorption in the area between 2400CM$^{-1}$ and 2300CM$^{-1}$ with the increase in carbon dioxide concentration within the vials.

EXAMPLE 3

Figure 7:
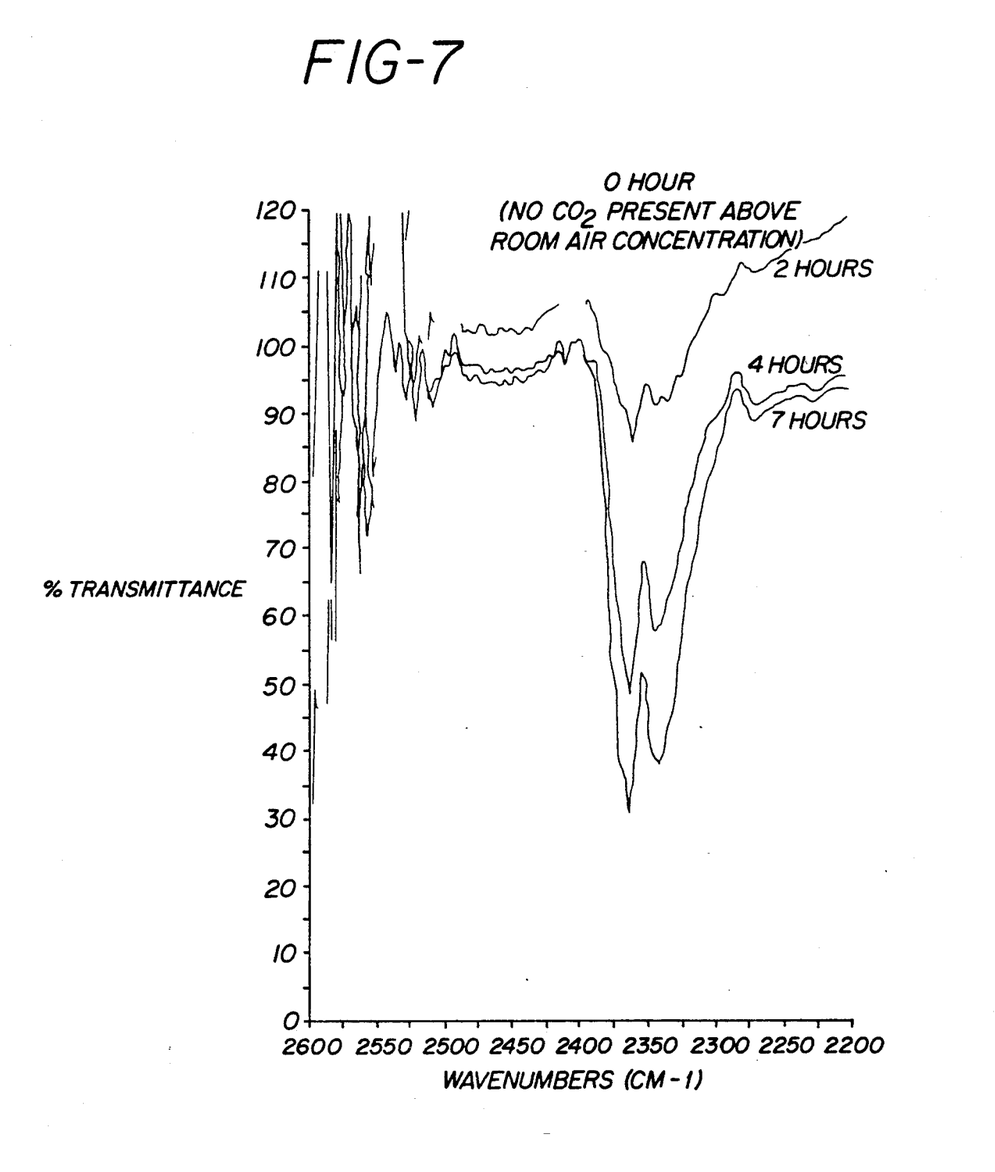
FIGS. 7 and 8 show $CO_2$ production resulting from organism metabolism as detected by infrared analysis.

The increase in infrared absorption as correlated with organism growth is shown in FIG. 7.

30 mls of tryptic soy broth (TSB) contained in two polymethylpentene bottles was sterilized by autoclaving. One bottle was inoculated at 0 hours with approximately one-half ml of an overnight *E.coli* culture. The other bottle was not inoculated and was used as a reference. The bottles were scanned sixty times each at the intervals indicated in FIG. 7. The data presented in FIG. 7 represent the scan of the inoculated bottle minus the scan of the uninoculated bottle. The bottles were incubated at 37° C. between readings. A clear correlation can be seen between organism growth and infrared absorption in the area of carbon dioxide absorption.

Figure 8:
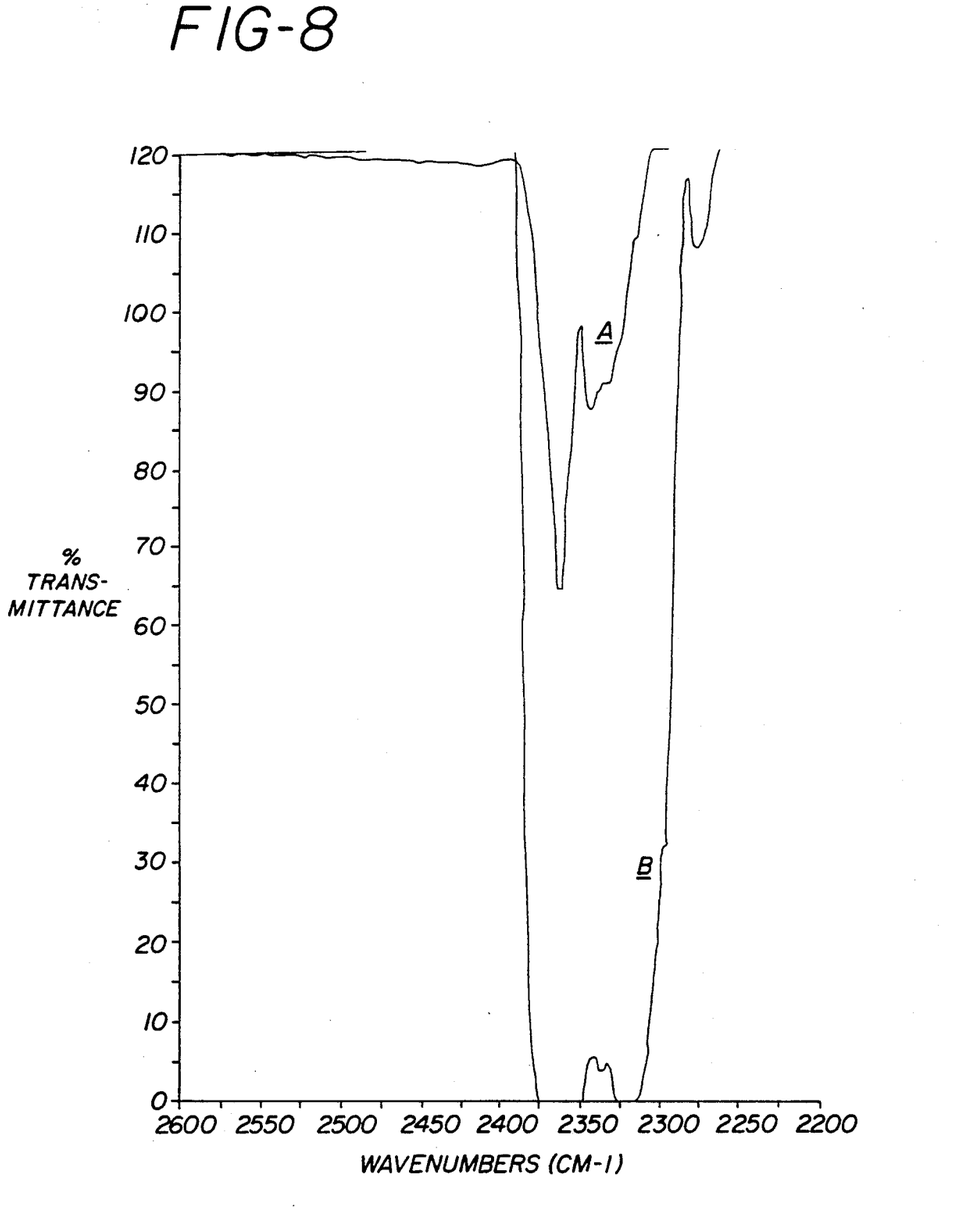

FIG. 8 shows a scan of a soda lime glass vial containing sterile medium and a scan of a soda lime vial containing sterile medium with *Clostridium perfringens* present in the stationary phase following extended incubation. Both infrared scans were referenced against a scan of a soda lime glass vial open to room air. All scans were performed sixty times in the Nicolet spectrophotomer. The vial containing *C. perfringens* exhibits a much larger carbon dioxide signal than the vial containing the culture medium alone.

While the method and apparatus of the present invention have been described with respect to the detection of bacteria, the method and apparatus may be used to detect biological activity broadly, including cell organisms, tissue culture cells, yeasts, enzymatic reactions and the like. Variations of the invention described herein will be apparent to those skilled in the art. It is intended, therefore, that the invention be limited only by the scope of the appended claims.

What is claimed is:

1. Apparatus for non-invasively analyzing a sample for the presence of microorganisms, said apparatus comprising:

a sealable container for receiving the sample; a growth medium including a carbon source which may be metabolized to produce carbon dioxide in the container; the container being made of a material selected from the group consisting of borosilicate glass, soda lime glass and polymethylpentene and having a sufficient size to have a head space above the level of the growth medium;

means for sealing the sample, medium and a gas within the head space in the container from an outside environment;

means for exposing the container and thereby the medium and the sample to conditions conducive to microorganism metabolism to provide carbon dioxide to the headspace;

means for producing an infrared beam passing through said container and said gas within the head space, and means for receiving the infrared beam after passing through the container and the gas within the head space for detecting the infrared absorbence of carbon dioxide in the gas within the head space.

2. Apparatus in accordance with claim 1 wherein said container has an infrared transmittance of at least about one percent at a wave number region of from about 2300 CM$^{-1}$ to 2400 CM$^{-1}$.

3. Apparatus in accordance with claim 1 wherein said material is borosilicate glass.

4. Apparatus in accordance with claim 1 wherein said material is soda lime glass.

5. Apparatus in accordance with claim 1 wherein said material is polymethylpentene.

6. A method for analyzing a sample for the presence of microorganisms, said method comprising:

placing the sample into a closed container together with a growth medium including a carbon source which may be metabolized to produce carbon dioxide, the container being made of a material selected from the group consisting of borosilicate glass, soda lime glass, and polymethylpentene;

exposing the container with the medium and the sample therein to conditions conductive to the occurrence of metabolism for a period sufficient to cause production of $CO_2$ by microorganism metabolism of said carbon source, and therefore non-invasively determining the presence of $CO_2$ in a gaseous atmosphere in the container above said medium by measuring the infrared absorbence of said gaseous atmosphere within said container by passing an infrared beam through said container and said gaseous atmosphere and detecting the infrared absorbence of the carbon dioxide in said gaseous atmosphere.

7. A method in accordance with Claim 6 wherein said container has an infrared transmittance of at least about one percent at a wave number region of from about 2300 CM$^{-1}$ to 2400 CM$^{-1}$.

8. A method in accordance with Claim 6 wherein said material is borosilicate glass.

9. A method in accordance with Claim 6 wherein said material is soda lime glass.

10. A method in accordance with Claim 6 wherein said material is polymethylpentene.

11. A method in accordance with Claim 6 wherein said container is revolved during infrared absorbance measurement.

* * * * *